(12) United States Patent
Chang et al.

(10) Patent No.: US 7,354,735 B2
(45) Date of Patent: Apr. 8, 2008

(54) NUCLEIC ACID ENCODING FLUORESCENT PROTEIN CONSTRUCTS AND METHODS FOR DETECTING APOPTOSIS

(75) Inventors: Donald Choy Chang, Kowloon (HK); Qian (Kathy) Luo, Kowloon (HK)

(73) Assignee: Hong Kong University of Science and Technology, Hong Kong SAR (HK)

( * ) Notice: Subject to any disclaimer, the term of this patent is extended or adjusted under 35 U.S.C. 154(b) by 0 days.

(21) Appl. No.: 10/341,979

(22) Filed: Jan. 15, 2003

(65) Prior Publication Data

US 2004/0002128 A1 Jan. 1, 2004

Related U.S. Application Data

(63) Continuation-in-part of application No. 09/866,447, filed on May 24, 2001, now abandoned.

(30) Foreign Application Priority Data

May 24, 2002 (CN) ............................. 02 1 20427

(51) Int. Cl.
 *C12P 21/06* (2006.01)
(52) U.S. Cl. .................. 435/69.1; 435/7.1; 435/252.3; 435/325; 435/320.1; 435/7.2; 435/7.4; 530/300; 530/350; 424/192.1; 536/23.1
(58) Field of Classification Search ............... 435/325, 435/7.2, 7.4, 7.1, 252.3, 320; 424/192.1; 536/23.1, 23.4, 23.6; 530/350
See application file for complete search history.

(56) References Cited

U.S. PATENT DOCUMENTS

| | | | | |
|---|---|---|---|---|
| 5,981,200 | A | 11/1999 | Tsien et al. ............... 435/7.4 |
| 6,077,707 | A | 6/2000 | Tsien et al. ............... 435/325 |
| 6,403,374 | B1 | 6/2002 | Tsien et al. ............... 435/325 |
| 6,410,255 | B1 | 6/2002 | Pollok et al. ............... 435/23 |
| 6,416,959 | B1 | 7/2002 | Giuliano et al. ............ 435/7.2 |
| 6,469,154 | B1 | 10/2002 | Tsien et al. ............... 536/23.5 |
| 6,596,499 | B2 * | 7/2003 | Jalink .................... 435/7.1 |
| 2002/0164674 | A1 | 11/2002 | Tsien et al. | |
| 2003/0087328 | A1 | 5/2003 | Pollok et al. | |
| 2003/0143650 | A1 | 7/2003 | Steward et al. | |
| 2003/0143651 | A1 | 7/2003 | Steward et al. | |
| 2004/0072270 | A1 | 4/2004 | Fernandez-Salas et al. | |

FOREIGN PATENT DOCUMENTS

WO   WO 97/28261   *   8/1997
WO   WO 00/73437   A1   12/2000

OTHER PUBLICATIONS

Onuki et al., "Confirmation by FRET in individual living cells of the absence of significant amyloid B-mediated caspase 8 activation"; Biochemistry, vol. 99, No. (Nov. 12, 2002).

Cubitt et al., "Understanding, improving and using green fluorescent proteins", Techniques, TIBS 20, Elsevier Science Ltd. 0968 (Nov. 1995).
Mitra et al., "Flourescence resonance energy transfer between blue-emitting and red-shifted excitation derivatives of the green fluorescent protein"; Gene, 173, 13-17 (1996).
Xu et al., "Detection of programmed cell death using fluorescence energy transfer"; Nucleic Acids Research, vol. 26, No. 8, pp. 2034-2035 (1998).
Pollock et al., Using CFP in FRET-based applications; Cell Biology, vol. 9 (Feb. 1999).
Tawa et al.; Quantitative analysis of fluorescent caspase substrate cleavage in intact cells and identification of novel inhibitors of apoptosis; Cell Death and Differentiation, vol. 8, pp. 30-37 (2001).
Luo et al., "Application of the Fluorescence Resonance Energy Transfer Method for Studying the Dynamics of Caspase-3 Activation during UV-induced Apoptosis in Living HeLa Cells"; Biochemical and Biophysical Research Communications, vol. 283, pp. 1054-1060 (2001).
Rehm et al., "Single-Cell Fluorescence Resonance Energy Transfer Analysis Demonstrates That Caspase Activation during Apoptosis Is a Rapid Process"; The Journal of Biological Chemistry, vol. 277, No. 27, pp. 24506-24514 (Jul. 2002).
Kohl et al.; "A protease assay for two-photon crosscorrelation and FRET analysis based solely on fluorescent proteins", Biophysics, vol. 99, No. 19, pp. 121161-12166 ((Sep. 2002).
Heim, R., et al., Engineering Green Fluorescent Protein for Improved Brightness, Longer Wavelengths and Fluorescence Resonance Energy Transfer, Current Biology (1995), 178-182, 6, Current Biology Ltd ISSN.
Mahajan, N.P., et al., Novel Mutant Green Fluorescent Protein Protease Substrates Reveal the Activation of Specific Caspases During Apoptosis, Chemistry & Biology (1999), 401-409, 6, Elsevier Science Ltd ISSN.
Tyas, L., et al., Rapid Caspase-3 Activation During Apoptosis Revealed Using Fluorescence-Resonance Energy Transfer, EMBO Reports (2000), 266-270, 1(3), European Molecular Biology Organization.
Latif, R., et al., Fluorescent Probes: Looking Backward and Looking Forward, Thyroid (2000), 407-412, 10(5), Mary Ann Liebert, Inc.
Jones, J., et al., Development and Application of a GFP-FRET Intracellular Caspase Assay for Drug Screening [In Process Citation], Journal of Biomolecular Screening (2000), 307-318, 5(5), The Society for Biomolecular Screening.
Xiang Xu, Amy L.V. Gerard, Betty C.B., Huang, David C. Anderson, Donald G. Payan, and Ying Luo, *Detection of programmed cell death using fluorescence energy transfer*, Nucleic Acids Research, 1998, vol. 26, No. 8, pp. 2034-2035.

* cited by examiner

*Primary Examiner*—Hope Robinson
(74) *Attorney, Agent, or Firm*—Baker & McKenzie LLP

(57) ABSTRACT

Isolated nucleic acids encoding a fluorescent protein construct that detect apoptosis are disclosed. The isolated nucleic acids contain a donor-acceptor pair of green fluorescent proteins and a peptide linker containing a substrate sequence encoding a cleavage site of a caspase. The linker is flanked with at least one glycine pair. Expression constructs, isolated host cells and gene delivery vehicles containing these isolated nucleic acids are also disclosed.

21 Claims, 8 Drawing Sheets

NUCLEIC ACID ENCODING FLUORESCENT PROTEIN CONSTRUCTS AND METHODS FOR DETECTING APOPTOSIS

CROSS-REFERENCE TO RELATED APPLICATION

This is a continuation-in-part of application Ser. No. 09/866,447 entitled "GFP-based Methods for Detecting Apoptosis" filed on 24 May 2001, now abandoned. Additional priority is claimed from the People's Republic of China Patent Application No. 02120427.6, filed on 24 May 2002.

REFERENCE TO SEQUENCE LISTING

Two copies of the "Sequence Listing" in computer readable form in compliance with 37 C.F.R. §1.821 to 1.825 are enclosed. The sequence listing information recorded in computer readable form is identical to the written on paper sequence listing, and incorporated herein by reference.

BACKGROUND OF THE INVENTION

The present invention relates to compositions and methods for detecting apoptosis or programmed cell death.

Throughout this disclosure, various publications are referenced by first author and date, within parentheses, patent number or publication number. The complete bibliographic reference is given at the end of the application for several of the references. The disclosures of these publications are hereby incorporated by reference into the present disclosure to more fully describe the state of the art to which this application pertains.

Apoptosis, also called programmed cell death ("PCD"), is a very important cellular process that plays a vital role in maintaining the normal physiological function of the organism [1,2]. For example, when DNA is damaged in a cell and cannot be repaired, the cell will enter apoptosis to avoid the formation of abnormalities in the tissue. In addition, the process of apoptosis is used in the thymus to eliminate self-reactive T cells to avoid auto-immunity. Apoptosis must be precisely regulated in order to maintain the proper functioning of our body. For example, failure to activate apoptosis can cause cancer or auto-immune diseases [3]. On the other hand, excessive activity of apoptosis can cause great damage to the organism; it can lead to many neurodegenerative diseases such as Huntington's disease and Alzheimer's disease [4, 5].

Since many important diseases, including cancer, AIDS, auto-immune diseases and neurodegenerative diseases are related to defective or excessive programmed cell death, drugs that can either facilitate or block programmed cell death can both be potentially useful in treating many diseases. Thus, there is a great interest in studying the process of apoptosis on a molecular basis. The signaling pathways that direct the programmed cell death process are very complicated [6-8]. Many external signals can trigger the initiation of apoptosis, including UV-irradiation, activation of the "death domain" via the TNF (tumor necrosis factor) receptor, treatment of hormone (e.g., glucocorticoid) or chemotherapy drugs (e.g., camptothecin) [6-9]. As for the internal signals, it is known that apoptosis is the outcome of a programmed cascade of intracellular events, which are centered on the activation of a class of cysteine proteases called "caspases" [7, 10]. Caspases are death proteases that are homologous to each other [22]. They are highly conserved through evolution and can be found from humans to insect, nematodes and hydra. [23-25]. Over a dozen caspases have been identified in humans, two thirds of which are believed to function in apoptosis [25, 26].

All known caspases possess an active-site cysteine and cleave substrates at Asp-Xxx bonds. The distinct specificity of each caspase is determined by the four residues amino terminus to the cleavage site [27]. Caspases are divided into subfamilies based on substrate preference, extent of sequence identity and structural similarities. For a review of the biochemistry of apoptosis and the role of caspases, see Hengartner, M. (2000) Nature 407:770-776.

At present, there exist a variety of techniques that can detect the process of apoptosis at different stages. For example, the terminal stage of apoptosis can be assayed by morphological changes of the cell (such as the presence of apoptotic bodies). Before that, apoptosis can be assayed by DNA fragmentation using either gel analysis or the TUNEL technique [11]. Early stages of apoptosis can be assayed by the turnover of PS (phosphatidylserine) in the membrane using an Annexin V-FITC labeled protein [12], or by detecting the activation of caspase-3 using a fluorescent dye linking to a substrate peptide [13]. All of these techniques, however, have certain limitations. For example, gel analysis can only be applied to an extract of cells, not to a single cell or intact cells. The TUNEL method can only be applied to fixed celled, not living cells. Annexin V can only detect events at the outer cell surface, not inside the cell. The caspase probe using a peptide linked fluorescence dye also has its own limitations. First, this probe cannot penetrate the cell membrane, and thus, it is typically used to assay cell extract. It is not an in vivo assay. Secondly, the fluorescent change resulting from caspase cleavage involves mainly a shift of the emission spectrum in the dye rather than a total destruction of the fluorescence. Its sensitivity is limited. Thus, a need exists for efficient and accurate compositions and methods to detect programmed cell death. This invention satisfies this need and provides related advantages as well.

SUMMARY OF THE INVENTION

At present, there is a strong need to develop efficient methods that can detect the activation of the apoptotic process in the living cells. The detection method of this invention is based on the fact that the process of programmed cell death involves the activation of a series of intracellular proteases called "caspases." Substrates of these caspases often share a consensus recognition and cleavage amino acid sequence called "substrate sequence". Using genetic engineering techniques, molecular probes were generated to assay the caspase activity by inserting a gene encoding a substrate sequence into a linker which connects two flourescent protein molecules of different color and exhibits a fluorescent resonance energy transfer (FRET) property. When this engineered gene was expressed in a cell, its gene product (i.e., the protein of the probe) was a substrate of the specific caspase and was cleaved by the caspase upon its activation. Following this molecular cleavage, the FRET property of the probe was destroyed. And thus, the activation of the caspase was detected by monitoring the change of the fluorescent property of the fluorscent probe.

Unlike conventional techniques for detecting apoptosis, the invention provides a highly sensitive yet simple assay that detects the early stages of apoptosis. The development of the inventive molecular probes takes advantage of three different technologies, some of which have only recently become available. They are: (1) the development of the GFP technology, (2) the known substrate sequence of the caspase family, and (3) the method of FRET (fluorescent resonance energy transfer).

A fluorescent protein construct to detect protease or caspase activated apoptosis is provided by this invention. The construct contains a donor fluorescent protein, an acceptor fluorescent protein, and a linker peptide positioned in between the donor and acceptor. The linker peptide contains a substrate sequence of a caspase. This invention also provides nucleic acids encoding the fluorescent protein construct, expression constructs comprising the nucleic acids as well as gene delivery vehicles containing these nucleic acids.

These compositions are useful in a method for detecting caspase or protease activated apoptosis by culturing a sample of host cells containing the nucleic acids and/or proteins described above under conditions suitable for excitation of the donor fluorescent protein and detecting the fluorescence property in the sample, wherein the presence of apoptosis in the cells of the sample results in a change in the degree of fluorescence resonance energy transfer between the donor protein and the acceptor protein.

This invention also provides tools to facilitate future studies leading to a better understanding of the mechanisms regulating apoptosis and will assist in the discovery and development of new drugs to combat many important diseases.

DETAILED DESCRIPTION OF THE INVENTION

Figure 1:
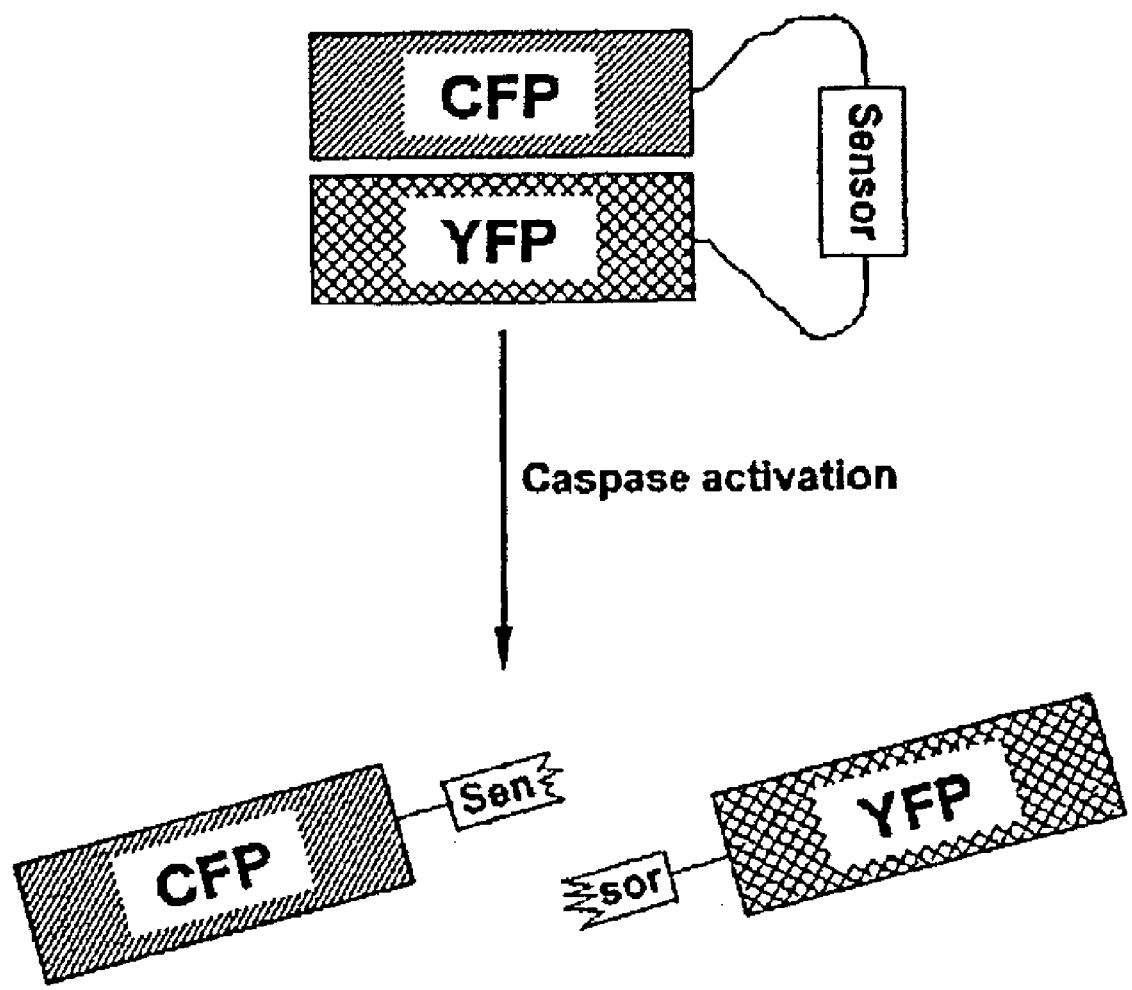
FIG. 1 shows the principle of design of an inter-GFP ("GFP") probe. This probe is constructed by linking a cyan color Green Fluorescent Protein molecule (CFP) with a yellow color GFP molecule (YFP) using a short peptide containing the substrate sequence of the caspase (which is called the "sensor" here). When these two GFP molecules are linked together, the phenomenon of "fluorescent resonance energy transfer" (FRET) takes place. When cells enter apoptosis, the activate caspase cleaves the substrate peptide (i.e., the "sensor") linking the two GFP molecules. When the two GFP molecules become separated, no FRET can take place.
Figure 2:
FIG. 2 shows SDS-PAGE analysis of the purified recombinant FRET probes. The polyhistidine-tagged FRET fusion proteins were expressed in bacteria and purified on a Ni-NTA column. Each sample containing approximately 5.2 μg of protein was analyzed by elecrophoresis in a 12% SDS-PAGE gel, followed by staining with Coomassie Blue.

The practice of the present invention employs, unless otherwise indicated, conventional techniques of molecular biology (including recombinant techniques), microbiology, cell biology, biochemistry and immunology, which are within the skill of the art. Such techniques are explained fully in the literature. These methods are described in the following publications. See, e.g. Sambrook et al. MOLECULAR CLONING: A LABORATORY MANUAL, $2^{nd}$ edition (1989); CURRENT PROTOCOLS IN MOLECULAR BIOLOGY (F. M. Ausubel et al. eds. (1987)); the series METHODS IN ENZYMOLOGY (Academic Press, Inc.); PCR: A PRACTICAL APPROACH (M. MacPherson et al. IRL Press at Oxford University Press (1991)); PCR 2: A PRACTICAL APPROACH (M. J. MacPherson, B. D. Hames and G. R. Taylor eds. (1995)); ANTIBODIES, A LABORATORY MANUAL (Harlow and Lane eds. (1988)); and ANIMAL CELL CULTURE (R. I. Freshney ed. (1987)).

Definitions

As used herein, certain terms may have the following defined meanings.

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The terms "polynucleotide" and "nucleic acid" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-, double-stranded and triple helical molecules, a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules.

The term "peptide" is used in its broadest sense to refer to a compound of two or more subunit amino acids, amino acid analogs, or peptidomimetics. The subunits may be linked by peptide bonds. In another embodiment, the subunit may be linked by other bonds, e.g ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

The term "genetically modified" means containing and/or expressing a foreign gene or nucleic acid sequence which in turn, modifies the genotype or phenotype of the cell or its progeny. In other words, it refers to any addition, deletion or disruption to a cell's endogenous nucleotides.

As used herein, "expression" refers to the process by which polynucleotides are transcribed into mRNA and translated into peptides, polypeptides, or proteins. If the polynucleotide is derived from genomic DNA, expression may include splicing of the mRNA, if an appropriate eucaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Sambrook et al. (1989) supra). Similarly, an eucaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described below for constructing vectors in general.

A "promoter" is a region on a DNA molecule to which an RNA polymerase binds and initiates transcription. The nucleotide sequence of the promoter determines both the nature of the enzyme that attaches to it and the rate of RNA synthesis. In the present disclosure the term "promoter" is used to mean a polynucleotide that includes not only the RNA polymerase binding site but also all other contiguous sequence elements that interact with factors which modulate transcription initiation, such as repressors or inducers of transcription. Thus a "promoter" as defined here, is a polynucleotide that contains all of the sequence information required to regulate gene expression in the same way as the native element in the chromosome.

"Under transcriptional control" is a term well understood in the art and indicates that transcription of a polynucleotide sequence, usually a DNA sequence, depends on its being operatively linked to an element which contributes to the initiation of, or promotes, transcription. "Operatively linked" refers to a juxtaposition wherein the elements are in an arrangement allowing them to function.

The term "expression construct" means a polynucleotide comprising a promoter element operatively linked to a gene. The expression construct can be formatted in a variety of ways such as in a gene delivery vehicle or inserted into a chromosome of a cell. The term is intended to refer to promoter-gene fusions produced by any method including, but not limited to recombinant DNA techniques, homologous recombination, targeted insertion of a gene or promoter element or random insertion of a gene or promoter element. A "gene delivery vehicle" is defined as any molecule that can carry inserted polynucleotides into a host cell. Examples of gene delivery vehicles are liposomes, biocompatible polymers, including natural polymers and synthetic polymers; lipoproteins, polypeptides; polysaccharides; lipopolysaccharides; artificial viral envelopes; metal particles; and bacteria, viruses, such as baculovirus, adenovirus and retrovirus, bacteriophage, cosmid, plasmid, fungal vectors and other recombination vehicles typically used in the art which have been described for expression in a variety of eucaryotic and prokaryotic hosts, and may be used for gene therapy as well as for simple protein expression.

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g, viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "viral vector" is defined as a recombinantly produced virus or viral particle that comprises a polynucleotide to be delivered into a host cell, either in vivo, ex vivo or in vitro.

Examples of viral vectors include retroviral vectors, adenovirus vectors, adeno-associated virus vectors and the like. In aspects where gene transfer is mediated by a retroviral vector, a vector construct refers to the polynucleotide comprising the retroviral genome or part thereof, and a transgene. As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g. WO 95/27071. Ads are easy to grow and do not require integration into the host cell genome. Recombinant Ad-derived vectors, particularly those that reduce the potential, for recombination and generation of wild-type virus, have also been constructed. See, WO 95/00655 and WO 95/11984. Wild-type AAV has high infectivity and specificity integrating into the host cell's genome. See, Hermonat and Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as STRATAGENE™ (La Jolla, Calif.) and PROMEGA BIOTECH™ (Madison, WI). In order to optimize expression and/or in vitro transcription, it may be necessary to remove, add or alter 5', and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include several non-viral vectors, including DNA/liposome complexes, and targeted viral protein-DNA complexes. Liposomes that also comprise a targeting antibody or fragment thereof can be used in the methods of this invention. To enhance delivery to a cell, the nucleic acid or proteins of this invention can be conjugated to antibodies or binding fragments thereof which bind cell surface antigens, e.g, TCR, CD3 or CD4.

As used herein, a "reporter gene" is a polynucleotide encoding a protein whose expression by a cell can be detected and quantified. Thus, a measurement of the level of expression of the reporter is indicative of the level of activation of the promoter element that directs expression of the reporter gene.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a polymerase chain reaction (PCR) reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions of about 6×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed. A polynucleotide or polynucleotide region (or a polypeptide or polypeptide region has a certain percentage (for example, 80%, 85%, 90%, or 95%) of "sequence identity" to another sequence meant that, when aligned, that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. A preferred program for aligning polynucleotide and polypeptide sequences to determine percent homology is CLUSTALW, using default parameters. This program is available on the world wide web at a variety of sites such as the institute for Biological Computing at Washington University in Saint Louis, Mo., the Human Genome Sequencing Center of the Baylor College of Medicine in Houston, Tex. and the Pasteur Institute in Paris, France .

A "biological equivalent" of a reference polynucleotide is one characterized by possessing at least 75%, or at least 80%, or at least 90% or at least 95% sequence identity as determined using a sequence alignment program under default parameters, correcting for ambiguities in the sequence data and changes in nucleotide sequence that do not alter function. A "biologically equivalent" polynucleotide can also be isolated by hybridization under moderate or stringent hybridization conditions. In addition to sequence similarity or hybridization with reference polynucleotides, the biologically equivalent polynucleotide has the same or similar biological function as the reference polynucleotide.

A variety of software programs are available in the art to identify biologically equivalent polynucleotides without an undue amount of experimentation. Non-limiting examples of these programs are BLAST™ family programs including BLASTN™, BLASTP™, BLASTX™ TBLASTN™, and TBLASTX™ (BLAST is available from the worldwide web), FASTA™, COMPARE™, DOTPLOT™, BESTFIT™, GAP™, FRAMEALIGN™, CLUSTALW™, and PILEUP™. These programs can be obtained commercially in a comprehensive package of sequence analysis software such as GCG Inc.'s WISCONSINPACKAGE™. Other similar analysis and alignment programs can be purchased from various providers such as DNA Star's MEGALIGN™, or the alignment programs in GENEJOCKEY™. Alternatively, sequence analysis and alignment programs can be accessed throughout the world wide web at sites such as the CMS Molecular Biology Resource. Any sequence database that contains DNA or protein sequences corresponding to a gene or a segment thereof can be used for sequence analysis. Commonly employed data bases include but are not limited to GENBANK®, EMBL™, DDBJ™, PDB™, SWISS-PROT™, EST™, STS™, GSS™, and HTGS™. Sequence similarity can be discerned by aligning the tag sequence against a DNA sequence database. Alternatively, the tag sequence can be translated into six reading frames; the predicted peptide sequences of all possible reading frames are then compared to individual sequences stored in a protein database such as is done using the BLASTX™ program.

Parameters for determining the extent of homology set forth by one or more of the aforementioned alignment programs are well established in the art. They include but are not limited to p value, percent sequence identity and the percent sequence similarity. P value is the probability that the alignment is produced by chance. For a single alignment, the p value can be calculated according to Karlin et al. (1990) Proc. Natl. Acad. Sci. USA 87: 2246. For multiple alignments, the p value can be calculated using a heuristic approach such as the one programmed in BLAST. Percent sequence identify is defined by the ratio of the number of nucleotide or amino acid matches between the query sequence and the known sequence when the two are optimally aligned. The percent sequence similarity is calculated in the same way as percent identity except one scores amino acids that are different but similar as positive when calculating the percent similarity.

"In vivo" gene delivery, gene transfer, gene therapy and the like as used herein, are terms referring to the introduction of a vector comprising an exogenous polynucleotide directly into the body of an organism, such as a human or non-human mammal, whereby the exogenous polynucleotide is introduced to a cell of such organism in vivo.

The term "isolated" means separated from constituents, cellular and otherwise, in which the polynucleotide, peptide, polypeptide, protein, antibody, or fragments thereof, are normally associated with in nature. For example, with respect to a polynucleotide, an isolated polynucleotide is one that is separated from the 5' and 3' sequences with which it is normally associated in the chromosome. As is apparent to those of skill in the art, a non-naturally occurring polynucleotide, peptide, polypeptide, protein, antibody, or fragments thereof, does not require "isolation" to distinguish it from its naturally occuring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions, are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eucaryotic cell in which it is produced in nature.

"Host cell," or "genetically modified cell" are intended to include any individual cell or cell culture which can be or have been recipients for vectors or the incorporation of exogenous nucleic acid molecules, polynucleotides and/or proteins. It also is intended to include progeny of a single cell, and the progeny may not necessarily be completely identical (in morphology or in genomic or total DNA complement) to the original parent cell due to natural, accidental, or deliberate mutation. The cells may be procaryotic or eucaryotic, and include but are not limited to bacterial cells, yeast cells, animal cells, and mammalian cells, e.g., murine, rat, simian or human.

A "subject" is a vertebrate, preferably a mammal, more preferably a human. Mammals include, but are not limited to, murines, simians, humans, farm animals, sport animals, and pets.

A "control" is an alternative subject or sample used in an experiment for comparison purposes. A control can be "positive" or "negative". For example, where the purpose of the experiment is to determine a correlation of an altered expression level of a gene with a particular type of cancer, it is generally preferable to use a positive control (a subject or a sample from a subject, carrying such alteration and exhibiting syndromes characteristic of that disease), and a negative control (a subject or a sample from a subject lacking the altered expression and clinical syndrome of that disease).

The term "culturing" refers to the in vitro propagation of cells or organisms on or in media of various kinds. It is understood that the descendants of a cell grown in culture may not be completely identical (morphologically, genetically, or phenotypically) to the parent cell. By "expanded" is meant any proliferation or division of cells.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin REMINGTON'S PHARM. SCI., 15th Ed. (Mack Publ. Co., Easton (1975)).

An "effective amount" is an amount sufficient to effect beneficial or desired results. An effective amount can be administered in one or more administrations, applications or dosages.

Green Fluorescence Protein ("GFP") is a highly useful protein that has greatly facilitated the studies of cell and molecular biology in the last few years. GFP was originally discovered from the jellyfish *Aequorea victoria* by Shimomura et al. in 1962 [14] and its gene was cloned and sequenced by Prasher et al. in 1992 [15]. The GFP molecule contains a fluorophore generated through an oxygen-dependent cyclization reaction involving three amino acids [16]. Recently, it was found that the GFP gene can be expressed in a wide variety of cells to produce an endogenous fluorescent protein, without requiring exogenous substrates or coenzymes [16-18]. Utilizing this endogenous fluorescence property, GFP has become a very powerful tool for studying regulation of gene expression. It has also been used as a fusion tag for monitoring protein localization and movement within living cells [16-18].

The invention provides GFP-based molecular probes that are sensitive to proteases and more particularly, different members of caspases. Each caspase has its unique recognition and cleavage amino acid sequence (i.e., "substrate sequence") [19]. For example, the substrate sequence for caspase-3 is DEVD (Asp-Glu-Val-Asp) (SEQ ID NO:11). Table 1 lists several caspases and their substrate sequence.

TABLE 1

| Proteases | Alternative names | Recognition/cleavage sequence | Protein substrates |
| --- | --- | --- | --- |
| caspase-1 | ICE | Try-Val-Ala-Asp (YVAD) (SEQ. ID. NO.: 12) | Pro-IL-1β |
| caspase-2 | ICH-1/Nedd2 | Asp-Glu-His-Asp (DEHD) (SEQ. ID. NO.: 13) | PARP |
| caspase-3 | CPP32/Yama/apopain | Asp-Glu-Val-Asp (DEVD) (SEQ. ID. NO.: 11) | PARP, DNA-PK, SREBP1,2, rho-G |
| caspase-4 | TX/ICH-2./ICErel-II | Trp/Leu-Glu-His-Asp (W/LEHD) (SEQ. ID. NO.: 14) | |
| caspase-5 | TY/ICErel-III | Trp/Leu-Glu-His-Asp (W/LEHD) (SEQ. ID. NO.: 15) | |
| caspase-6 | Mch2 | Val-Glu-His-Asp (VEHD) (SEQ. ID. NO.: 16) | LaminA |
| caspase-7 | Mch3/ICE-LAP3/CMH-1 | Asp-Glu-Val-Asp (DEVD) (SEQ. ID. NO.: 11) | PARP, pro-caspase 6, SREBP1,2 |
| caspase-8 | MACH/FLICE/Mch5 | Leu-Glu-Thr-Asp (LETD) (SEQ. ID. NO.: 17) | PARP |
| caspase-9 | ICE-LAP6/Mch6 | Leu-Glu-His-Asp (LEHD) (SEQ. ID. NO.: 18) | PARP |
| caspase-10 | FLICE2/Mch4 | | |
| caspase-11 | ICH-3 | | |
| caspase-12 | DRONC | | |
| caspase-13 | ERICE | | |
| caspase-14 | MICE | Asp-Glu-Val-Asp (DEVD) (SEQ. ID. NO.: 11) | |

PARP:poly(ADP-ribose)polymerase

Reference:
Cryns V. and Yuan J. *Genes Dev* 11, 1551-1570, 1998.
Cohen G. M. *Biochem J.* 326(Pt1), 1-16, 1997.
Negata S. *Cell* 88, 355-365, 1997.
Thornberry N. A., *J. Biol. Chem.* 272, 17907-17911, 1977.

In order to develop a practically useful probe to detect caspase activation in living cells several technical issues were addressed and overcome, for example, (1) selection of the best matching pair of GFP as donor and acceptor; (2) optimizing the linker design so that the effect of FRET is maximized before the linker is cleaved by the caspase; and (3) optimizing the linker design so that the substrate sequence at the linker is easily accessible by the caspase.

One apsect of the invention is a fluorescent protein construct to detect protease or caspase activated apoptosis or programmed cell death, wherein the construct contains 1) a donor fluorescent protein; 2) an acceptor fluorescent protein; and 3) a peptide linker containing a substrate sequence of the protease or caspase. The linker is positioned between linking the donor fluorescent protein and the acceptor fluorescent protein. As used herein, the term "caspase activity apoptosis or programmed cell death" shall mean apoptosis or programmed cell death caused by a set of cysteine proteases that are specifically activated in apoptotic cells. The constructs are particularly suited to detect protease or caspase activated apoptosis of the type identified in Table 1, above or a caspase selected from the group consisting of caspase-3, caspase-6, caspase-8 and caspase-9. Substrate sequences for the enzymes are known in the art, see for example, Table 1, supra.

In one aspect, at least one of the donor or acceptor is isolated from a biological organism. In another aspect, at least one of donor fluorescent protein or the acceptor fluorescent protein is an Aequorea-related fluorescent protein or a mutant or variant thereof. Alternatively, both of the donor fluorescent protein and the acceptor fluorescent protein are an Aequorea-related fluorescent protein or a mutant or variant thereof. Aequorea-related proteins and functional mutants thereof are well known to those of skill in the art and commercially available. See, e.g., U.S. Pat. No. 5,981,200 (and references cited therein), the teachings of which are incorporated herein by reference. It is intended, although not always explicitly recited that at least the donor and/or fluorescent proteins can be wild-type, mutant or biological equivalents thereof. Biological equivalents can be determined using sequenced based homology comparison or by hybridization under moderate or stringent conditions as defined above.

The two GFP molecules can have different "colors" (fluorescent properties) such that the emission spectrum of the first GFP (the donor) overlaps with the absorption spectrum of the second GFP (the acceptor). Since these two GFP molecules are linked together, the phenomenon of "fluorescent resonance energy transfer" (FRET) takes place [20]. That is, when the donor molecule is excited by light of appropriate wavelength, energy is transferred to the acceptor molecule and it will emit fluorescent light. In one aspect, this FRET phenomenon is useful to detect activation of the caspase and when cells enter apoptosis, the caspase is activated. The activated caspase cleaves the substrate peptide linking the two GFP molecules. When the two GFP molecules become separated, no FRET takes place. Thus, there will be no emission of light from the acceptor molecule when the donor molecule is excited. This change of fluorescent property can be detected using various optical devices (e.g., a fluorescence microscope or a spectrofluorometer). Applicant has determined that the following GFP color pairs are particularly suited for the subject invention:

BFP-GFP (blue-green); CFP GFP (cyano-green); CFP YFP (cyano-yellow); BFP YFP (blue-yellow); and YFP-CFP (yellow-cyano).

The specially designed probe consists of two GFP molecules linked together by a short peptide containing the substrate or cleavage sequence of the caspase. (See FIG. 1). The peptide linker is preferably between 4 and 30 amino acids, or between 6 and 30, or between 8 and 30, or between 8 and 20, or between 16 and 30, or between 16 and 20. In one aspect the linker is 16 amino acids or greater in length. In a further aspect, the linker is flanked with one or two glycine pairs, e.g., GXXXXG (SEQ ID NO: 22) or GGXXXXGG (SEQ ID NO: 23). In an alternative embodiment, the peptide linker is more than 50% containing one or more amino acid selected from the group consisting of glycine, serine and threonine.

This invention also provides a nucleic acid encoding for the fluorescent protein constructs described herein and an expression construct containing one or more of these nucleic acids. These can be further encompassed within a gene delivery vehicle. The protein constructs, nucleic acids, expression constructs and gene delivery vehicles of this invention can be provided in isolated form, in a carrier, such as a pharmaceutically acceptable carrier, or within a host cell. The host cell, in turn, can be provided in isolated form, or alternatively, provided in combination with a carrier such as a pharmaceutically acceptable carrier.

The nucleic acid molecules of this invention can be isolated or replicated using polymerase chain reaction ("PCR") (Perkin-Elmer). For example, the sequence can be chemically replicated using PCR (Perkin-Elmer) which in combination with the synthesis of oligonucleotides, allows easy reproduction of DNA sequences. The PCR technology is the subject matter of U.S. Pat. Nos. 4,683,195, 4,800,159, 4,754,065, and 4,683,202 and described in PCR: THE POLYMERASE CHAIN REACTION Mullis et al. eds, Birkhauser Press, Boston (1994) and references cited therein. Alternatively, one of skill in the art can use the sequences provided herein and a commercial DNA synthesizer to replicate the DNA. Accordingly, this invention also provides a process for obtaining the polynucleotides of this invention by providing the linear sequence of the polynucleotide, nucleotides, appropriate primer molecules, chemicals, such as enzymes and instructions for their replication and chemically replicating or linking the nucleotides in the proper orientation to obtain the polynucleotides. In a separate embodiment, these polynucleotides are further isolated. Still further, one of skill in the art can insert the nucleic acid into a suitable replication vector and insert the vector into a suitable host cell for replication and amplification. The DNA so amplified can be isolated from the cell by methods well-known to those of skill in the art. A process for obtaining nucleic acid molecules by this method is further provided herein as well as the nucleic acid molecules so obtained.

RNA can be obtained by using the isolated DNA and operatively linking it to a control region appropriate for the host cell and inserting it into a host cell. The DNA can be inserted by any appropriate method, e.g., by the use of an appropriate insertion vector or by electroporation. When the cell replicates and the DNA is transcribed into RNA; the RNA can then be isolated using methods well-known to those of skill in the art, for example, as set forth in Sambrook et al. (1989) supra.

The invention further provides the nucleic acid molecule operatively linked to a promoter of RNA transcription, as well as other regulatory sequences for replication and/or transient or stable expression of the DNA or RNA. In certain embodiments, cell-specific promoters are used for cell-specific expression of the inserted nucleic acid molecule. Vectors that contain a promoter or a promoter/enhancer, with termination codons and selectable marker sequences, as well as a cloning site into which an inserted piece of DNA can be operatively linked to that promoter are well-known in the art and commercially available. For general methodology and cloning strategies, see GENE EXPRESSION TECHNOLOGY, Goeddel ed., Academic Press, Inc. (1991) and references cited therein and VECTORS: ESSENTIAL DATA Series, Gacesa and Ramji, eds., John Wiley & Sons, N.Y. (1994), which contains maps, functional properties, commercial suppliers and a reference to GenEMBL accession number for various suitable vectors. Preferable, these vectors are capable of transcribing RINA in vitro or in vivo.

As noted above, a nucleic acid molecule of this invention can be operatively linked to a promoter, either an inducible or non-inducible promoter, of RNA transcription. These nucleic acid molecules are useful for the recombinant production of the fluorescent proteins and polypeptides or as vectors for diagnostic use. Accordingly, this invention also provides a vector (insertion, replication or expression vector) having inserted therein a nucleic acid molecule described above, for example, a viral vector, such as bacteriophage, baculovirus and retrovirus, or cosmids, plasmids, YACS, yeast and other recombinant vectors. Nucleic acid molecules are inserted into vector genomes by methods well-known in the art. For example, insert and vector DNA can both be exposed to a restriction enzyme to create complementary ends on both molecules that base pair with each other and which are then joined together with a ligase. Alternatively, synthetic nucleic acid linkers can be ligated to the insert DNA that corresponds to a restriction site in the vector DNA, which is then digested with a restriction enzyme that recognizes a particular nucleotide sequence. Additionally, an oligonucleotide containing a termination codon and an appropriate restriction site can be ligated for insertion into a vector containing, for example, some or all of the following: a selectable marker gene, such as neomycin gene for selection of stable or transient transfectants in mammalian cells; enhancer/promoter sequences from the immediate early gene of human cytomegalovirus (CMV) for high levels of transcription; transcription termination and RNA processing signals from SV40 for mRNA stability; SV40 polyoma origins of replication and ColEl for proper episomal replication; versatile multiple cloning sites; and T7 and SP6 RNA promoters for in vitro transcription of sense and anti-sense RNA.

An additional example of a vector construct of this invention is a bacterial expression vector including a promoter such as the lac promoter and for transcription initiation, the Shine-Dalgarno sequence and the start codon AUG (Sambrook et al. (1989) supra). Similarly, a eucaryotic expression vector is a heterologous or homologous promoter for RNA polymerase II, a downstream polyadenylation signal, the start codon AUG, and a termination codon for detachment of the ribosome. Such vectors can be obtained commercially or assembled using the sequences described herein. When a nucleic acid is inserted into a suitable host cell, e.g., a procaryotic or a eucaryotic cell and the host cell replicates, the protein can be recombinantly produced. Suitable host cells will depend on the vector and can include mammalian cells, animal cells, human cells, simian cells, insect cells, yeast cells, and bacterial cells constructed using well-known methods. See Sambrook et al. (1989) supra. In addition to the use of viral vector for insertion of exogenous nucleic acid into cells, the nucleic acid can be inserted into the host cell by methods well-known in the art such as transformation for bacterial cells; transfection using calcium phosphate precipitation for mammalian cells; or DEAE-dextran; electroporation; or microinjection. See Sambrook et al. (1989) supra for this methodology. Thus, this invention also provides a host cell, e.g., a mammalian cell, an animal cell (rat or mouse), a human cell, or a bacterial cell, containing a nucleic acid molecule encoding the fluorescent construct.

This invention also provides a method for detecting caspase-activated programmed cell death or apoptosis, by culturing a sample containing host cells of this invention under conditions suitable for excitation of the donor fluorescent protein and detecting a fluorescence property in the sample, wherein the presence of caspase activated programmed cell death in the cells of the sample results in a change in the degree of fluorescence resonance energy transfer between the donor protein and the acceptor protein. The assay method may also be used for quantification of the change in the degree of fluorescent energy transfer.

In another aspect, one can use the method to determine whether an agent modifies caspase activated programmed cell death in the sample by contacting the sample with the agent and then culturing the sample under conditions suitable for excitation of the donor fluorescent protein and determining a fluorescent property of the sample wherein an activity of the agent is determined by a change in the degree of the fluorescent property in the presence and absence of the agent. As used herein, the term "agent" includes but is not limited to a small molecule compound, a protein, a nucleic acid, a ribozyme, and antisense nucleic acid molecules. Agents can augment apoptosis or down-regulate apoptosis. An example of agents that down-regulate caspase activated apoptosis is acetyl-Asp-Glu-Val-Asp-aldehyde (AC-DEVD-CHO) a chemical derivative of SEQ ID NO: 11, exemplified herein. The method can be further modified by providing a second sample comprising the host cells of this invention, culturing the cells under conditions suitable for exciting the donor fluorescent protein and comparing the degree of fluorescence resonance energy transfer in two samples.

Also provided by this invention are kits for performing the above assays, wherein the kits comprise the nucleic acids and instructions for use.

EXPERIMENTAL EXAMPLES

Although the specific examples are directed to the construction of caspase-specific probes, it is apparent to one of skill in the art that any protease and its substrate can be substituted in the methods provided herein. Accordingly, the following examples are intended to illustrate, not limit, the invention.

Construction of the FRET Probes

A mammalian construct containing the CFP-YFP fusion gene was generated as the following: First, EYFP was amplified by PCR from pEYFP-C1 using 5'-primer KL-3 (5'-CCG GAA TTC ATG GTG AGC AAG GGC GAG G)(SEQ ID NO: 1) containing an EcoRI site, and 3'-primer KL-5 (5'-CCG GAA TTC TAT GGT GAG CAA GGG CGA GG) (SEQ ID NO: 2) with a BamHI site. Second, the PCR product was cloned down stream from the CFP gene between the EcoRI and BamHI sites in vector pECFP-C1 (CLONTECH™). The amino acid sequence of the linker connecting CFP and YFP is SGLRSRAQASNS (SEQ ID NO: 3).

The first FRET probe (sensor A) was generated by replacing the amino acids of RAQA in the linker region of CFP-YFP fusion gene with G G D E V D G G (SEQ ID NO: 4) containing the caspase-3 recognition motif. The double strand DNA encoding this polypeptide was synthesized by primer extension using oligo KL-6 (5'-GGA AGA TCT GGA GGC GAG GAG GTG GAT GGA GGC TCG AAT TCT CGG-3') (SEQ ID NO: 5) as a template and oligo KL-8 (5'-CCG AGA ATT-3') (SEQ ID NO: 6) as a primer. The DNA was then cloned into the linker region of CFP-YFP probe between the BglII and EcoRI sites. There were 16 amino acids in the linker region of sensor A between the CFP and YFP molecules and its sequence was SGLRSG-GDEVDGGSNS (SEQ ID NO: 7) with a corresponding nucleic acid sequence TCCGGACTCAGATCTGGAGGC-GACGAGGTGGATGGAGGCTCGAATTCT. The second FRET probe (sensor B) was made by replacing the amino acids of RAQA in the linker of CFP-YFP probe with G G S G G D E V D G G S G G (SEQ ID NO: 8). The double strand DNA of the insert was generated using oligo KL-7 (5'-GGA AGA TCT GGA GGC AGC GGA GGC GAG GAG GTG GAT GGA GGC AGC GGA GGC TCG AAT TCT CGG-3')(SEQ ID NO: 9) as a template and oligo KL-8 as a primer. Thus, sensor B had a longer linker (22 amino acids) between the two GFPs and its amino acids sequence was SGL-RSGGSGGDEVDGGSGGSNS (SEQ ID NO: 10), with a corresponding nucleic acid sequence TCCGGACTCA-GATCTGGAGGCAGCGGAGGCGACGAG-GTGGATGGAGGCAGCGGAGGCTCGAATTCT.

The bacterial version of the FRET probes were made by cloning the CFP-YFP fusion genes from the mammalian construct into vector pRSET-B (Invitrogen) between the NcoI and the blunt-ended HindIII sites. All the fusion proteins contain a poly-histidine tag at their N-terminus.

The Constructed FRET Probes can be cleaved by Caspase-3

Figure 3:
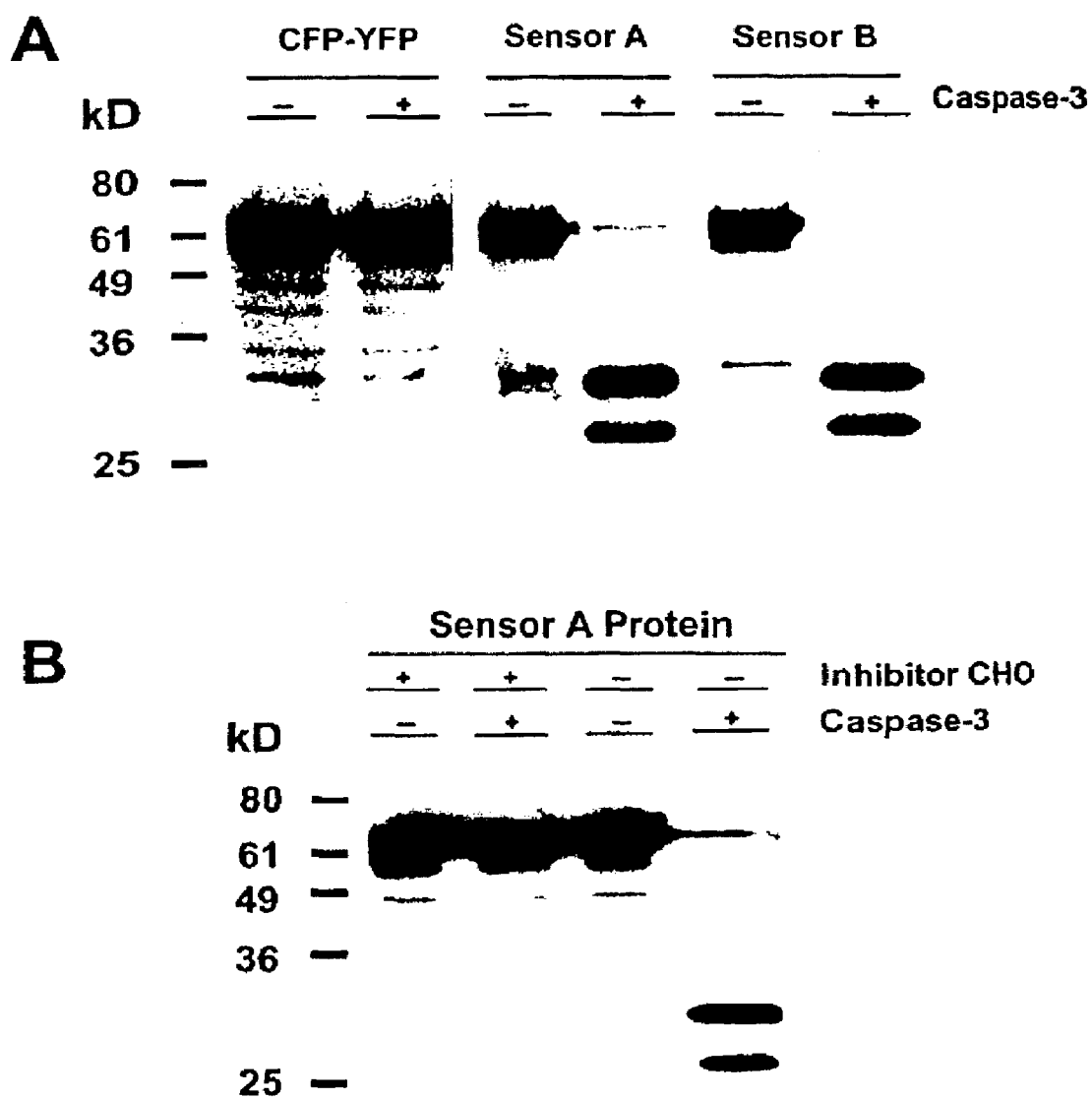
FIG. 3 shows Western blot analysis of caspase-3 cleavage. Purified FRET probes were incubated with caspase-3 in the reaction buffer at 37. degree. C. for 1-2 hrs. The reaction mixtures were separated on a SDS-PAGE and transferred onto a nitrocellulose membrane. The Protein blot was then probed with anti-GFP antibody (CLONTECH™). Acetyl-Asp-Glu-Val-Asp-aldehyde called CHO (AC-DEVD-CHO) is a chemical derivative of SEQ ID NO: 11 and a caspase-3 specific inhibitor.

To determine whether these FRET probes are sensitive to caspase-3 cleavage; the purified proteins were incubated with caspase-3 and then subjected to Western blot analysis. Antibodies were purchased from CLONTECH™. Result in FIG. 3A show that caspase-3 can cleave almost all the sensor A and sensor B protein, while no cleavage was seen for CFP-YFP fusion protein under the same condition. In the presence of caspase-3 inhibitor acetyl-Asp-Glu-Val-Asp-aldehyde (AC-DEVD-CHO) a chemical derivative of SEQ ID NO: 11, no FRET probe (sensor A) was cleaved, indicating that the cleavage is caspase-3 specific (FIG. 3B).

Optical Measurements Demonstrating the Changes in FRET Effect in Response to Caspase-3 Activity.

Figure 4:
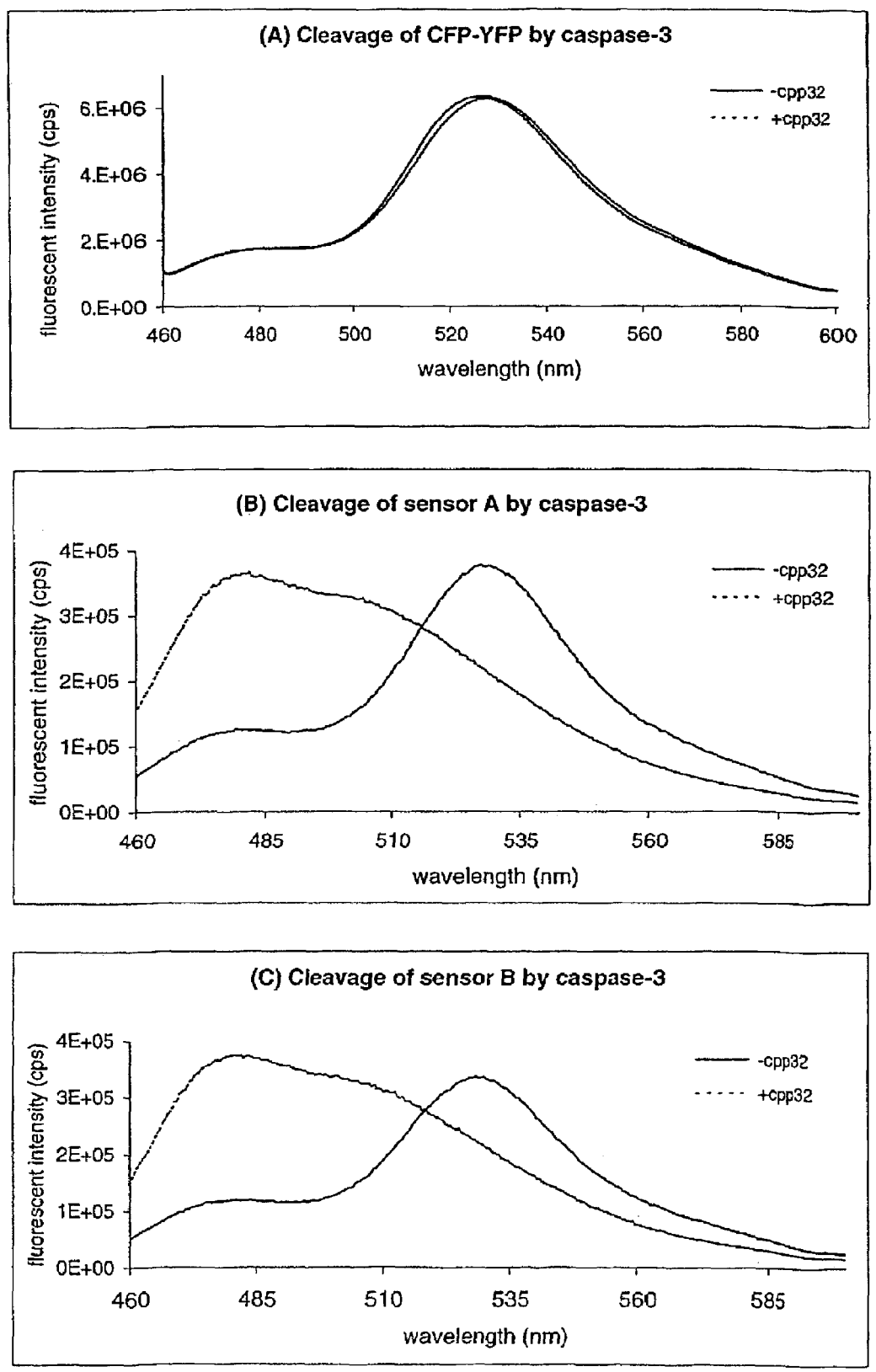
FIG. 4 shows caspase-3 treatment changed emission spectra of sensor A and B. The fluorescence emission spectrum of each probe was measured by a scanning spectrum analysis using a spectrofluorometer (SPEX 1681™). The excitation wavelength used to excite CFP in the probe was 433 nm. −cpp32: no caspase-3 in the reaction. +cpp32: caspase-3 was added into the reaction.

The fluorescent energy transfer from CYP to YFP in the FRET probes was measured using a spectrofluorometer. When CFP was excited in each probe at the excitation wavelength of 433 nm, very little emission light was detected from the FRET probes at the known emission wavelength for CFP (480 nm). Instead, a significant amount of emitted fluorescent light was detected at the emission wavelength of YFP which peaks at 526 nm (FIG. 4). This result indicated that an efficient energy transfer had occurred between the donor molecule of CFP and the acceptor molecule of YFP. It was then determined whether the FRET effect was sensitive to the caspase cleavage. The FRET probes were treated with caspase-3 and analyzed using a spectrofluorometer. It was found that caspase-3 treatment completely changed the emission spectra of both sensor A and B., resulting in a dramatic decrease in the emission peak of YFP and a significant increase in the emission peak of CFP (FIG. 4). As a control, no change for the emission spectrum was observed from the CFP-YFP fusion protein which lacks the substrate sequence (FIG. 4A). Based on spectra similar to FIG. 4, it was determined the YFP (526 nm)/CFP (480 nm) emission ratio for all three FRET probes before and after caspase treatment. This YFP/CFP ratio was used to quantify the FRET effect. It was found that, after incubating either sensor A or sensor B with caspase-3, the emission ratio of YFP/CFP was decreased by 4-5 fold, from 3.02 to 0.59 for sensor A and from 2.76 to 0.59 for sensor B.

Comparing the Sensitivity of Sensor A and Sensor B

Figure 5:
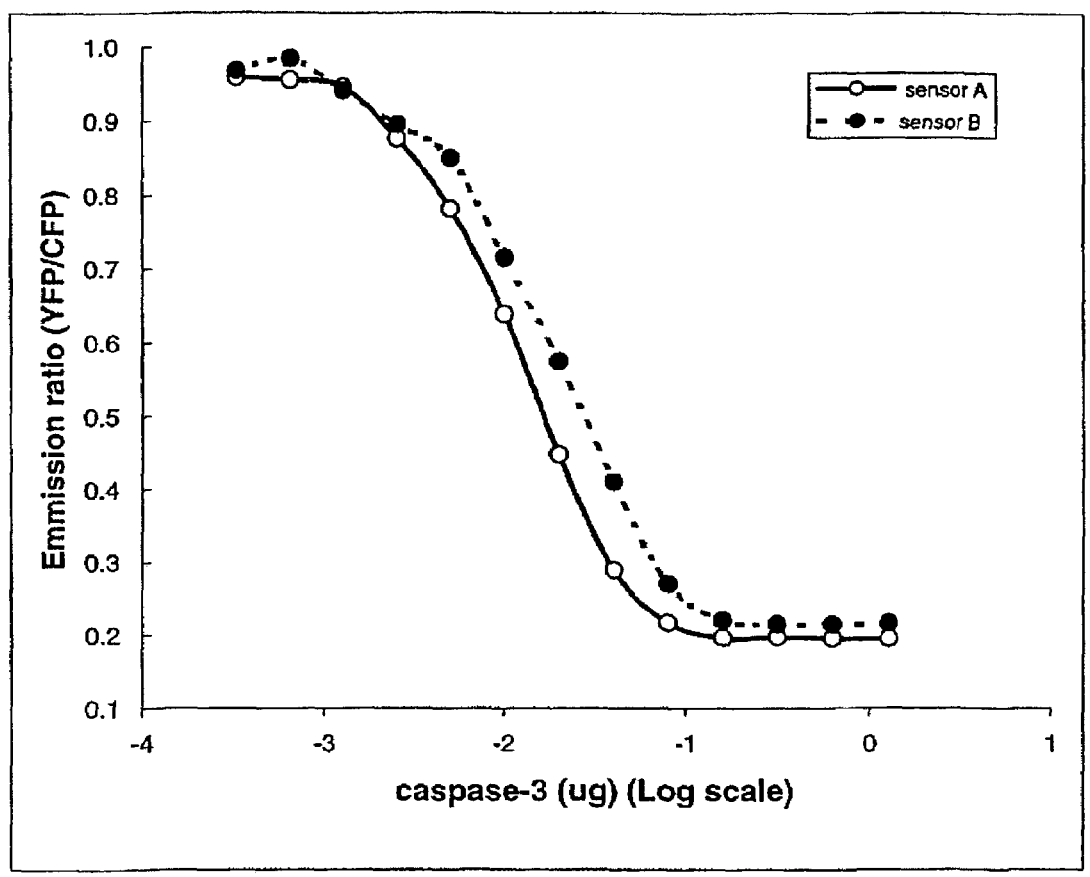
FIG. 5 shows dosage-dependent caspase-3 cleavage assay. Same amount of purified sensor A and sensor B protein was incubated with different amount of caspase-3 ranging from 0.3125 ng to 1.28 μg for 1 hr. The emission spectra of both YFP and CFP were measured for each sample at the end of reaction using a spectrofluorometer. The emission ratio (YFP/CFP) of each sample was normalized to the value of the ratio from a mock control with no caspase-3.

To compare the sensitivity of sensor A and sensor B on caspase-3 activity, a dosage-dependent caspase-3 cleavage assay was performed. In this experiment, 1.28 μg amount of the purified sensor A or sensor B protein was incubated with different amount of caspase-3 ranging from 0.3125 ng to 1.28 μg for 1 hour. The emission spectra of both YFP and CFP were measured for each sample at the end of the reaction using a spectrofluorometer. The emission ratio (YFP/CFP) of each caspase reaction was normalized with that of the mock control having no caspase-3 in the reaction. The results are shown in FIG. 5. It was found that both FRET probes were highly sensitive to caspase-3, although sensor A appeared to be slightly more sensitive than sensor B.

Using FET Probe to Detect Caspase-3 Activity in Living Cells During Apoptosis

Figure 6:
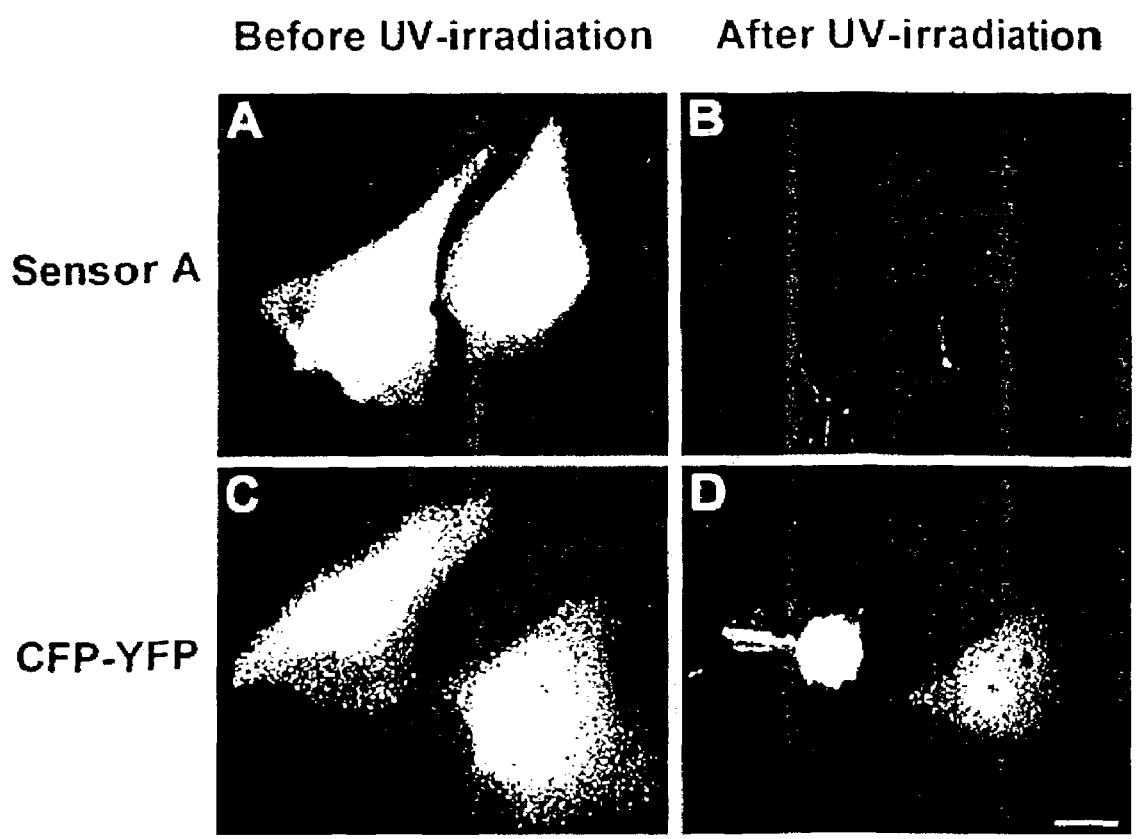
FIG. 6 shows imaging analysis of sensor A in HeLa cells under UV-treatment. HeLa cells expressing either sensor A or CFP-YFP fusion protein were induced to apoptosis by UV irradiation for 5 min. When the probe was excited at 440 nm, the fluorescent intensity of CFP (at 480±15 nm) and that of YFP (at 535±12.5 nm) from same cell before (A, C) and after (B, D) UV treatment was recorded using a cooled CCD imaging system. The representative ratio images of YFP/CFP are shown here. A significant FRET reduction is seen only in panel B from both cells expressing sensor A, but not in panel D with cells expressing the control fusion protein.
Figure 7:
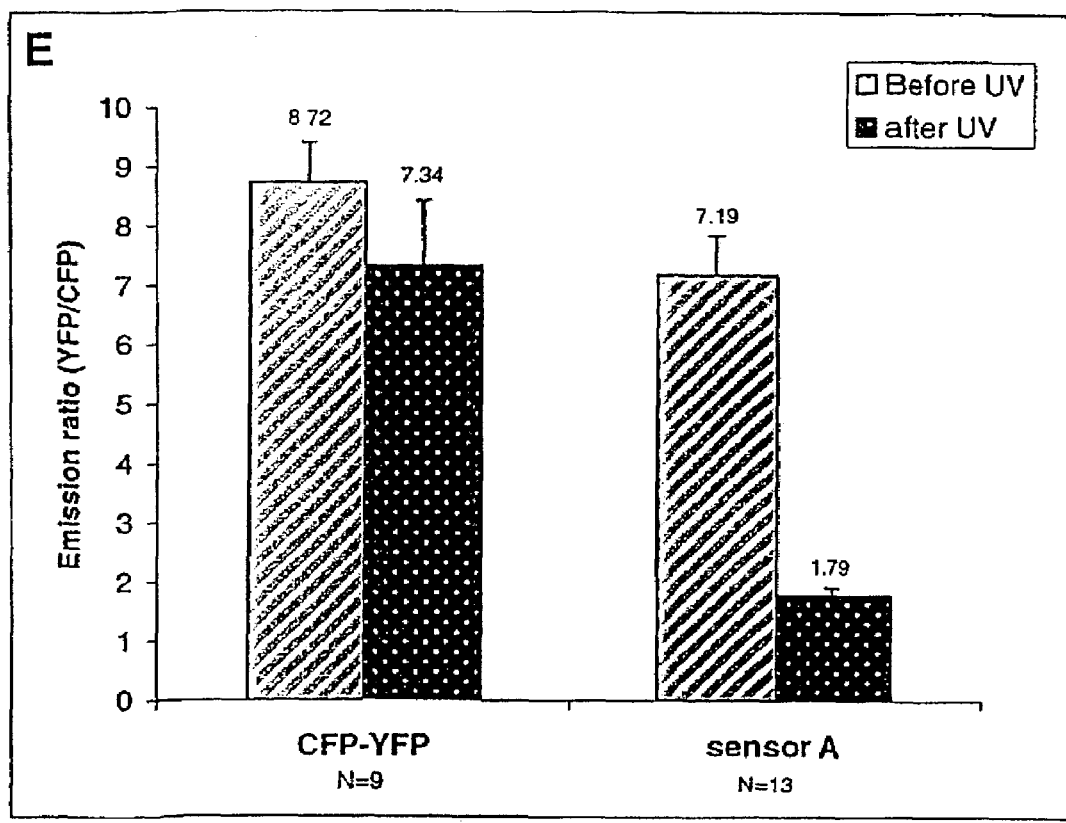
FIG. 7 is a statistic analysis of FRET changes during apoptosis. Images were recorded as described in FIG. 6. The fluorescent intensities of YFP and CFP were then determined from each image. The average values of YFP/CFP from 13 cells expressing sensor A and 9 cells expressing CFP-YFP fusion protein before and after UV-irradiation are plotted here. Nearly 4-fold reduction in the apoptotic cells expressing was found using the FRET probe but not in the control cells expressing the CFP-YFP fusion gene.

To test whether this FRET probe can be used to detect caspase activity in living cells, sensor A was expressed in HeLa cells and measured the FRET effect of the probe in single cells using a cooled CCD imaging system. The fluorescent images of the cell obtained from the emission wavelengths of CFP and YFP were recorded before and after UV treatment. A computer software (Metamorph, Universal Imaging) was used to generate a ratio image of YFP/CFP for each cell under different treatments. FIG. 6A shows two HeLa cells expressing sensor A before UV irradiation. At 3 hours after the UV treatment, these cells had entered apoptosis. The intensity of the YFP/CFP ratio image for these cells was found to decease dramatically (FIG. 6B). A similar experiment was performed on HeLa cells expressing the CFP/YFP probe which lacks the DEVD sequence, no significant change in the ratio image was observed before and after the UV treatment (FIG. 6C and FIG. 6D). The average YFP/CFP emission ratio changes was calculated for 13 apoptotic cells expressing sensor A, and found a nearly 4-fold reduction after UV treatment (FIG. 7). On the other hand, no significant reduction of the emission ratio was detected in nine control cells expressing CFP/YFP fusion construct (FIG. 7).

These results indicate that this FRET probe is a sensitive tool that can detect the activation of endogenous caspase-3 in living cells during apoptosis. Recently, sensor A was used to study the dynamics of caspase-3 activation during UV-induced apoptosis in living HeLa cells. It was found that, using this FRET probe, caspase-3 activation was clearly detected prior to any visible cell morphological changes. This result demonstrated that this FRET probe is a powerful tool for assaying the early stage of the apoptotic process.

Experimental Example #2

Generation of Caspase-8 Specific FRET Probes
Construction and Biochemical Characterization of Caspase-8 Probes In addition to the aforementioned caspase-3 specific probes, sensor A and sensor B, we have developed other FRET probes for detecting caspase-8 activation during apoptosis. These probes had a similar design as sensor A, with the CFP gene fused with the YFP gene via a peptide linker that contains the caspase-8 specific cleavage sequence IETD (Ile-Glu-Thr-Asp) (SEQ ID NO: 21). To explore the possibility that tandem IETD site might increase the cleavage efficiency of the probe to caspase-8, we introduced both single and double IETD sites into the sensor. That is, the sensor C8 had one IETD site, while the sensor C8A had two IETD sites, as shown below:

```
Sensor C8:  His(6x)-CFP-S-G-L-R-S-G-G-I-E-T-D-G-G-S-N-S-YFP              (SEQ. ID. NO.:20)

Sensor C8A: His(6x)-CFP-S-G-L-R-S-G-G-I-E-T-D-G-G-I-E-T-D-G-G-S-N-S-YFP (SEQ. ID. NO.:21)
```

Sensor C8: His(6x)-CFP-S-G-L-R-S-G-G-I-E-T-D-G-G-S-N-S-YFP (SEQ ID NO:20)

Sensor C8A: His(6x)-CFP-S-G-L-R-S-G-G-I-E-T-D-G-G-I-E-T-D-G-G-S-N-S-YFP (SEQ. ID. NO:21)

Figure 8:
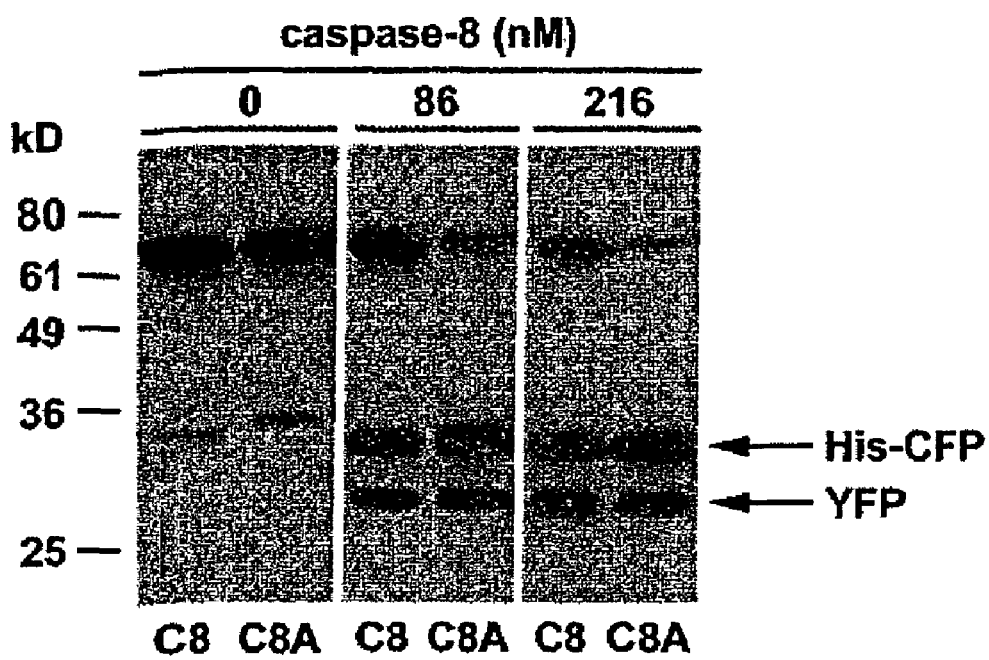
FIG. 8 is results of Western blot showing that purified sensor C8 and C8A protein (210 nM) could be cleaved by caspase-8 at two different (86 nM and 216 nM) concentrations. The positions of YFP and polyhistidine-tagged CFP are indicated by arrow.

The polyhistidine tagged sensor C8 protein was expressed in bacteria and purified using a Ni-NTA affinity column. The purified sensor C8 protein was incubated with caspase-8 enzyme and subjected to SDS-PAGE and Western blot analysis using anti-GFP and anti-histidine antibodies. The results are shown in FIG. 8. Before caspase-8 was applied, both sensor C8 and sensor C8A appeared as a single band with molecular weight at approximately 63 kDa, which was close to the expected molecular weight of the CFP and YFP fusion protein (see lane 1 and 2 in FIG. 8). After caspase-8 was added into the reaction, both sensors were cleaved into two bands that interacted with anti-GFP antibody. The top band had the expected molecular weight of His-CFP at around 33 kDa and was recognized by anti-histidine antibody, while the lower band had the molecular weight of YFP at around 30 kDa and did not show any interaction with the anti-histidine antibody. These results indicated that both sensor C8 and C8A could be cleaved by caspase-8 to release a CFP and a YFP molecule.

To compare the cleavage efficiency between the two C8 probes, the same amount of sensor C8 proteins (120 nM) were incubated with different amount of caspase-8 enzyme. The reaction mixtures were analyzed by Western blot experiment. Results in FIG. 8 showed that a larger fraction of sensor C8A protein was cleaved by the caspase-8 in comparison to sensor C8 (see FIG. 8, lane 3-6). Intensity analysis from the protein bands in lane 5 and 6 indicated that 95% of the sensor C8A protein was cleaved after incubation with caspase-8 (216 nM) for one hour (lane 6). While only 58% of the sensor C8 protein was cleaved under the same condition (lane 5). This result showed that the presence of double IETD site in sensor C8A had significantly increased its cleavage sensitivity by caspase-8.

Optical Measurement Shows that the Sensor C8A is a More Sensitive Probe for Detecting Caspase-8 Activity To determine whether there was an energy transfer between CFP and YFP in the caspase-8 sensors, we measured the emission spectra of the purified sensor protein using a spectrofluorometer. When the sensor C8 protein was excited at the excitation wavelength for CFP (433 nm), more fluorescence light was detected at the emission wavelength of YFP (526 nm) than at the emission wavelength of CFP (480 nm), indicating clearly that there was a FRET effect. The efficiency of the energy transfer was calculated using the emission ratio of YFP (526 nm)/CFP (480 nm) for both caspase-8 sensors. The measured FRET ratio for sensor C8 and C8A was 2.82 and 2.54, respectively.

Figure 9:
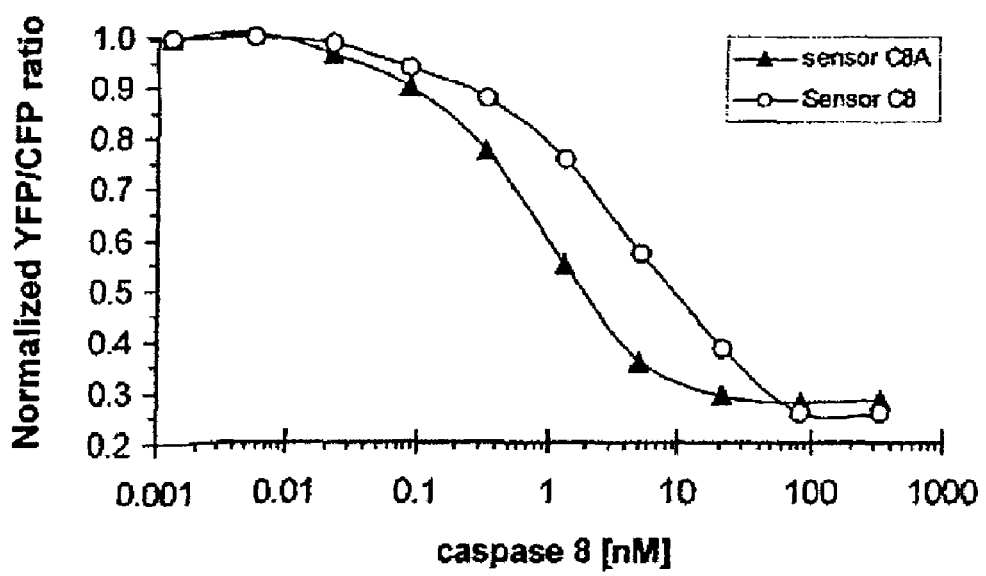
FIG. 9 is a dosage-dependent caspase-8 cleavage assay. A fixed amount of purified sensor C8 or C8A protein (22.45 nM) was incubated with different amount of caspase-8 for 1 hour. The emission spectra of each sample were measured at the end of reaction using a spectrofluorometer (excitation wavelength 433 nm). The emission ratio ($YFP_{526\ nm}/CFP_{480\ nm}$) was normalized against the value from a control sample that was not treated with caspase-8.

To compare the sensitivity of different sensors to caspase-8, we have performed a series of dosage-dependent caspase-8 cleavage assay. In these experiments, the same amount (22.45 nM) of sensor C8 and C8A protein was incubated with different amount of caspase-8 enzyme for one hour. Afterwards, we excited the reaction products with a light at the excitation wavelength for CFP (433 nm), and measured their emission spectra using a spectrofluorometer. The results are shown in FIG. 9, in which the relative emission ratio of YFP (526 nm)/CFP (480 nm) was plotted against the concentration of caspase-8. Here, the emission ratio (YFP/CFP) was normalized against that of the uncleaved sensor protein. We observed that about 0.71 nM of caspase-8 was needed to reduce 50% of the FRET effect for sensor C8A, while about 5-fold more caspase-8 (3.4 nM) was required to produce the same FRET reduction for sensor C8. These results suggested that sensor C8A containing double IETD sites is much more sensitive to the caspase-8 cleavage than sensor C8 which contains only a single IETD site.

It is to be understood that while the invention has been described in conjunction with the above embodiments, that the foregoing description and the following examples are intended to illustrate and not limit the scope of the invention. Other aspects, advantages and modifications within the scope of the invention will be apparent to those skilled in the art to which the invention pertains.

REFERENCES

1. Ken J F R, Wyllie A H and Currie A R, *Br J Cancer* 26, 239-257,1972.
2. Jacobson M D, Weil M and Raff M C, *Cell* 88, 347-354,1997.
3. Thompson C B, *Science* 267, 1456, 1995.
4. Kitamura Y et al., *Brain Res* 780, 260-269,1998; Mochizuki H, Mori H and Mizuno Y, *J Neural Transm Suppl* 50, 125-140,1997; Sabbah H N, Sharov V G and Goldstein S., *Ann Med Suppl* 1, 33-38, 1998.
5. Warner H R, Hodes R H and Pocinki K, *J Am Geriatr Soc* 45, 1140-1146; Tomei L D and Umansky S R, *Neurol Clin* 16, 735-745, 1998.
6. Ashkenazi A and Dixit V M, *Science* 281, 1305-1308, 1998.
7. Thornberry N A and Lazebnik Y, *Science* 281, 1312-1316,1998.
8. Evan G and Littlewood T, *Science* 281, 1322-1326, 1998; Adams J M and Corry S, *Science* 281, 1317-1322, 1998.
9. Nagata S, *Cell* 88, 355-365, 1997; Martin S J and Cotter T G, *Int Radiat Biol* 59, 1001-1016,1991.
10. Luo X et al, *Cell* 94,481-490, 1998.
11. Darzynkiewicz Z et al. *Cytometry* 27, 1-20, 1997.
12. Martin S J, et al, *J Exp Med* 182, 1545-1555, 1995.
13. CLONTECHniques 12, 4-6, 1997.
14. Shimomura O, Johnson F H and Saiga Y, *Aequorea J Cell Comp Physiol* 59, 223-227, 1962.
15. Prasher D C, Eckenrocde V K, Ward W W, Prendergast F G and Cormier M J, *Gene* 111, 229-233, 1992.
16. Tsien R Y *Annu Rev Biochem* 67, 509-544, 1998.
17. Chalfie M, Tu Y, Euskirchen G, Ward W W and Prasher D C, *Science* 263, 802-805, 1994.
18. Cubitt A B, Heim R., Adams S R, Boyd A E, Gross L A and Tsien R Y, *TIBS* 20, 448-455, 1995; Heim R, Prasher D C and Tsien R Y, *Proc Natl Acad Sci USA* 91, 12501-12504, 1994.
19. Cryns V and Yuan J, *Genes Dev* 11, 1551-1570, 1998; Cohen G M, *Biochem J* 326 (Pt1), 1-16, 1997.
20. Cubitt, A B et al. TIBS 20: 448-455 (1995).
21. Xu, X et al. *Nucleic Acids Res* 26, 2034-2035 (1998); Mahajan N P et al, *Chem Biol* 6, 401-409 (1999); Jones et al, *J Biomolecular Screening* 5, 307-3 16, (2000).
22. Alnermri, E. et al. *Cell* 87:171 (1996).
23. Budihardjo, I. et al. *Annu. Rev. Cell De., Biol* 15:269-290 (1999).
24. Cikala, M. et al. *Curr. Biol* 9:959-962 (1999).
25. Earnshaw, W. C., et al. *Annu. Rev. Biochem.* 68:383-424 (1999).
26. Thornberry, N. et al. *Science* 281:1312-1316 (1998).
27. Thornberry, N. et al. *J Biol. Chem.* 272:17907-17911 (1997).

---

SEQUENCE LISTING

<160> NUMBER OF SEQ ID NOS: 20

<210> SEQ ID NO 1
<211> LENGTH: 28
<212> TYPE: DNA
<213> ORGANISM: Aequorea victoria

<400> SEQUENCE: 1
ccggaattca tggtgagcaa gggcgagg                28

<210> SEQ ID NO 2
<211> LENGTH: 29
<212> TYPE: DNA
<213> ORGANISM: Aequorea victoria

<400> SEQUENCE: 2

```
ccggaattct atggtgagca agggcgagg                               29
```

<210> SEQ ID NO 3
<211> LENGTH: 12
<212> TYPE: PRT
<213> ORGANISM: mammalian

<400> SEQUENCE: 3

Ser Gly Leu Arg Ser Arg Ala Gln Ala Ser Asn Ser
1               5                   10

<210> SEQ ID NO 4
<211> LENGTH: 8
<212> TYPE: PRT
<213> ORGANISM: mammalian

<400> SEQUENCE: 4

Gly Gly Asp Glu Val Asp Gly Gly
1               5

<210> SEQ ID NO 5
<211> LENGTH: 45
<212> TYPE: DNA
<213> ORGANISM: mammalian

<400> SEQUENCE: 5

```
ggaagatctg gaggcgacga ggtggatgga ggctcgaatt ctcgg              45
```

<210> SEQ ID NO 6
<211> LENGTH: 9
<212> TYPE: DNA
<213> ORGANISM: mammalian

<400> SEQUENCE: 6

```
ccgagaatt                                                     9
```

<210> SEQ ID NO 7
<211> LENGTH: 16
<212> TYPE: PRT
<213> ORGANISM: mammalian

<400> SEQUENCE: 7

Ser Gly Leu Arg Ser Gly Gly Asp Glu Val Asp Gly Gly Ser Asn Ser
1               5                   10                  15

<210> SEQ ID NO 8
<211> LENGTH: 14
<212> TYPE: PRT
<213> ORGANISM: mammalian

<400> SEQUENCE: 8

Gly Gly Ser Gly Gly Asp Glu Val Asp Gly Gly Ser Gly Gly
1               5                   10

<210> SEQ ID NO 9
<211> LENGTH: 63
<212> TYPE: DNA
<213> ORGANISM: mammalian

<400> SEQUENCE: 9

```
ggaagatctg gaggcagcgg aggcgacgag gtggatggag gcagcggagg ctcgaattct   60
cgg                                                           63
```

```
<210> SEQ ID NO 10
<211> LENGTH: 22
<212> TYPE: PRT
<213> ORGANISM: mammalian

<400> SEQUENCE: 10

Ser Gly Leu Arg Ser Gly Gly Ser Gly Gly Asp Glu Val Asp Gly Gly
1               5                   10                  15

Ser Gly Gly Ser Asn Ser
            20

<210> SEQ ID NO 11
<211> LENGTH: 4
<212> TYPE: PRT
<213> ORGANISM: mammalian

<400> SEQUENCE: 11

Asp Glu Val Asp
1

<210> SEQ ID NO 12
<211> LENGTH: 4
<212> TYPE: PRT
<213> ORGANISM: mammalian

<400> SEQUENCE: 12

Tyr Val Ala Asp
1

<210> SEQ ID NO 13
<211> LENGTH: 4
<212> TYPE: PRT
<213> ORGANISM: mammalian

<400> SEQUENCE: 13

Asp Glu His Asp
1

<210> SEQ ID NO 14
<211> LENGTH: 5
<212> TYPE: PRT
<213> ORGANISM: mammalian

<400> SEQUENCE: 14

Trp Leu Glu His Asp
1               5

<210> SEQ ID NO 15
<211> LENGTH: 5
<212> TYPE: PRT
<213> ORGANISM: mammalian

<400> SEQUENCE: 15

Trp Leu Glu His Asp
1               5

<210> SEQ ID NO 16
<211> LENGTH: 4
<212> TYPE: PRT
<213> ORGANISM: mammalian

<400> SEQUENCE: 16

Val Glu His Asp
1
```

```
<210> SEQ ID NO 17
<211> LENGTH: 4
<212> TYPE: PRT
<213> ORGANISM: mammalian

<400> SEQUENCE: 17

Asp Glu Val Asp
1

<210> SEQ ID NO 18
<211> LENGTH: 4
<212> TYPE: PRT
<213> ORGANISM: mammalian

<400> SEQUENCE: 18

Leu Glu Thr Asp
1

<210> SEQ ID NO 19
<211> LENGTH: 4
<212> TYPE: PRT
<213> ORGANISM: mammalian

<400> SEQUENCE: 19

Leu Glu His Asp
1

<210> SEQ ID NO 20
<211> LENGTH: 4
<212> TYPE: PRT
<213> ORGANISM: mammalian

<400> SEQUENCE: 20

Asp Glu Val Asp
1
```

What is claimed is:

1. An isolated nucleic acid encoding a recombinant Aequorea victoria fluorescent protein that detects apoptosis, said fluorescent protein comprising:
   a) a donor fluorescent protein;
   b) an acceptor fluorescent protein;
   c) a peptide linker connecting said donor fluorescent protein to said acceptor fluorescent protein, wherein said peptide linker contains a cleavage site of a caspase, said peptide linker comprises SEQ ID NO: 23, and said cleavage site is flanked on each side with at least one glycine pair wherein XXXX represents a sequence selected from the group consisting of SEQ ID NO: 12, SEQ ID NO: 13, SEQ ID NO: 14, SEQ ID NO: 15, SEQ ID NO: 16, SEQ ID NO: 17; SEQ ID NO: 18, and SEQ ID NO: 19.

2. The isolated nucleic acid of claim 1, wherein said fluorescent protein has a FRET ratio of acceptor fluorescence over donor fluorescence greater than 2.5.

3. The isolated nucleic acid of claim 1, wherein the FRET ratio is reduced 4 to about 5 fold in the presence of active caspase cleavage.

4. The isolated nucleic acid of claim 1, wherein said peptide linker is SEQ ID NO: 24.

5. The isolated nucleic acid of claim 4, wherein said peptide linker is SEQ ID NO: 26.

6. The isolated nucleic acid of claim 1, wherein said peptide linker contains a sequence of SEQ ID NO: 25.

7. The isolated nucleic acid of claim 6, wherein said peptide linker is a sequence of SEQ ID NO: 20.

8. The isolated nucleic acid of claim 1, wherein said peptide linker comprises two caspase cleavage sites.

9. The isolated nucleic acid of claim 8, wherein said peptide linker is SEQ ID NO: 21.

10. The isolated nucleic acid according to claim 1, wherein the donor protein is selected from the group consisting of CFP, GFP, YFP and BFP and the acceptor protein is selected from the group consisting of GFP, YFP, and CFP.

11. The isolated nucleic of claim 10 wherein said donor protein is CFP and said acceptor protein is YFP.

12. An expression construct comprising an isolated nucleic acid of claim 1.

13. An isolated host cell transfected with the expression construct of claim 12.

14. An isolated host cell comprising an isolated nucleic acid of claim 1.

15. A gene delivery vehicle comprising an isolated nucleic acid of claim 1.

16. A stable cell line comprising an isolated nucleic acid of claim 1.

17. The stable cell line of claim 16, wherein said stable cell line is a HeLa cell line.

18. An isolated nucleic acid encoding a fluorescent protein construct comprising:
   a) a donor fluorescent protein;
   b) an acceptor fluorescent protein; and
   c) a peptide linker connecting said donor fluorescent protein and said acceptor fluorescent protein, wherein said peptide linker is selected from the group consisting of SEQ ID NO: 7 and SEQ ID NO: 10.

19. An isolated nucleic acid encoding a fluorescent protein construct comprising:
   a) a donor fluorescent protein;
   b) an acceptor fluorescent protein; and
   c) a peptide linker connecting said donor fluorescent protein and said acceptor fluorescent protein, wherein said peptide linker is selected from the group consisting of SEQ ID NO: 20 and SEQ ID NO: 21.

20. An isolated nucleic acid encoding a fluorescent protein construct comprising:
   a) a donor fluorescent protein;
   b) an acceptor fluorescent protein; and
   c) a peptide linker connecting said donor fluorescent protein and said acceptor fluorescent protein, wherein said peptide linker is SEQ ID NO: 8.

21. A method of identifying an apoptosis inducing compound comprising:
   a) culturing the stable cell line of claim 17,
   b) exposing said stable cell line to a compound, and
   c) measuring FRET fluorescence wherein a reduction in FRET fluorescence as compared to FRET fluorescence in the absence of the compound, is indicative of an apoptosis inducing compound.

* * * * *

UNITED STATES PATENT AND TRADEMARK OFFICE
CERTIFICATE OF CORRECTION

| | |
|---|---|
| PATENT NO. | : 7,354,735 B2 |
| APPLICATION NO. | : 10/341979 |
| DATED | : April 8, 2008 |
| INVENTOR(S) | : Chang et al. |

It is certified that error appears in the above-identified patent and that said Letters Patent is hereby corrected as shown below:

Column 16, line 7, that portion of the sequence reading "GGC GAG GAG" should read --GGC GAC GAG--.

Column 16, line 21, that portion of the sequence reading "AGA TCT GGA GGC AGC GGA GGC GAG GAG GTG" should read --AGA TCT GGA GGC AGC GGA GGC GAC GAG GTG--.

Column 18, line 12, "(SEQ ID NO: 21)" should read --(SEQ ID NO: 19)--.

Column 25, line 53, before "SEQ ID NO: 12" insert: --SEQ ID NO: 11--.

Column 20, line 47, cancel the text beginning with "SEQUENCE LISTING" to and ending "Asp Glu Val Asp 1" in column 25, line 39, and insert the following sequence listing:

SEQUENCE LISTING

```
<160>   26

<210>   1
<211>   28
<212>   DNA
<213>   Artificial

<220>
<223>   Primer

<400>   1
ccggaattca tggtgagcaa gggcgagg                          28
```

UNITED STATES PATENT AND TRADEMARK OFFICE
CERTIFICATE OF CORRECTION

| | | |
|---|---|---|
| PATENT NO. | : 7,354,735 B2 | Page 2 of 16 |
| APPLICATION NO. | : 10/341979 | |
| DATED | : April 8, 2008 | |
| INVENTOR(S) | : Chang et al. | |

It is certified that error appears in the above-identified patent and that said Letters Patent is hereby corrected as shown below:

```
<210>  2
<211>  29
<212>  DNA
<213>  Artificial

<220>
<223>  Primer

<400>  2
ccggaattct atggtgagca agggcgagg                               29

<210>  3
<211>  12
<212>  PRT
<213>  Artificial

<220>
<223>  Linker

<400>  3

Ser Gly Leu Arg Ser Arg Ala Gln Ala Ser Asn Ser
1               5                   10
```

UNITED STATES PATENT AND TRADEMARK OFFICE
CERTIFICATE OF CORRECTION

| | | |
|---|---|---|
| PATENT NO. | : 7,354,735 B2 | Page 3 of 16 |
| APPLICATION NO. | : 10/341979 | |
| DATED | : April 8, 2008 | |
| INVENTOR(S) | : Chang et al. | |

It is certified that error appears in the above-identified patent and that said Letters Patent is hereby corrected as shown below:

```
<210>  4
<211>  8
<212>  PRT
<213>  Artificial

<220>
<223>  Linker

<400>  4

Gly Gly Asp Glu Val Asp Gly Gly
1               5

<210>  5
<211>  45
<212>  DNA
<213>  Artificial

<220>
<223>  Primer

<400>  5
ggaagatctg gaggcgacga ggtggatgga ggctcgaatt ctcgg            45
```

UNITED STATES PATENT AND TRADEMARK OFFICE
CERTIFICATE OF CORRECTION

| | | |
|---|---|---|
| PATENT NO. | : 7,354,735 B2 | |
| APPLICATION NO. | : 10/341979 | |
| DATED | : April 8, 2008 | |
| INVENTOR(S) | : Chang et al. | |

It is certified that error appears in the above-identified patent and that said Letters Patent is hereby corrected as shown below:

```
<210>  6
<211>  9
<212>  DNA
<213>  Artificial

<220>
<223>  Primer

<400>  6
ccgagaatt                                                                              9

<210>  7
<211>  16
<212>  PRT
<213>  Artificial

<220>
<223>  Linker

<400>  7

Ser Gly Leu Arg Ser Gly Gly Asp Glu Val Asp Gly Gly Ser Asn Ser
1               5                   10                  15
```

UNITED STATES PATENT AND TRADEMARK OFFICE
CERTIFICATE OF CORRECTION

PATENT NO.         : 7,354,735 B2
APPLICATION NO. : 10/341979
DATED              : April 8, 2008
INVENTOR(S)        : Chang et al.

It is certified that error appears in the above-identified patent and that said Letters Patent is hereby corrected as shown below:

```
<210>  8
<211>  14
<212>  PRT
<213>  Artificial

<220>
<223>  Linker

<400>  8
Gly Gly Ser Gly Gly Asp Glu Val Asp Gly Gly Ser Gly Gly
1               5                   10

<210>  9
<211>  63
<212>  DNA
<213>  Artificial

<220>
<223>  Primer

<400>  9
ggaagatctg gaggcagcgg aggcgacgag gtggatggag gcagcggagg ctcgaattct    60
cgg                                                                  63
```

UNITED STATES PATENT AND TRADEMARK OFFICE
CERTIFICATE OF CORRECTION

| | |
|---|---|
| PATENT NO. | : 7,354,735 B2 |
| APPLICATION NO. | : 10/341979 |
| DATED | : April 8, 2008 |
| INVENTOR(S) | : Chang et al. |

It is certified that error appears in the above-identified patent and that said Letters Patent is hereby corrected as shown below:

```
<210>  10
<211>  22
<212>  PRT
<213>  Artificial

<220>
<223>  Linker

<400>  10

Ser Gly Leu Arg Ser Gly Gly Ser Gly Gly Asp Glu Val Asp Gly Gly
 1               5                  10                  15

Ser Gly Gly Ser Asn Ser
                20

<210>  11
<211>  4
<212>  PRT
<213>  Artificial

<220>
<223>  Linker
```

UNITED STATES PATENT AND TRADEMARK OFFICE
CERTIFICATE OF CORRECTION

| | |
|---|---|
| PATENT NO. | : 7,354,735 B2 |
| APPLICATION NO. | : 10/341979 |
| DATED | : April 8, 2008 |
| INVENTOR(S) | : Chang et al. |

It is certified that error appears in the above-identified patent and that said Letters Patent is hereby corrected as shown below:

```
<400>   11

Asp Glu Val Asp
1

<210>   12
<211>   4
<212>   PRT
<213>   Artificial

<220>
<223>   Linker

<400>   12

Tyr Val Ala Asp
1

<210>   13
<211>   4
<212>   PRT
<213>   Artificial

<220>
<223>   Linker
```

UNITED STATES PATENT AND TRADEMARK OFFICE
CERTIFICATE OF CORRECTION

| | | |
|---|---|---|
| PATENT NO. | : 7,354,735 B2 | Page 8 of 16 |
| APPLICATION NO. | : 10/341979 | |
| DATED | : April 8, 2008 | |
| INVENTOR(S) | : Chang et al. | |

It is certified that error appears in the above-identified patent and that said Letters Patent is hereby corrected as shown below:

```
<400>  13

Asp Glu His Asp
1

<210>  14
<211>  4
<212>  PRT
<213>  Artificial

<220>
<223>  Linker

<220>
<221>  MISC_FEATURE
<222>  (1)..(1)
<223>  Wherin Xaa is either Trp or Leu.

<400>  14

Xaa Glu His Asp
1
```

UNITED STATES PATENT AND TRADEMARK OFFICE
CERTIFICATE OF CORRECTION

| | |
|---|---|
| PATENT NO. | : 7,354,735 B2 |
| APPLICATION NO. | : 10/341979 |
| DATED | : April 8, 2008 |
| INVENTOR(S) | : Chang et al. |

It is certified that error appears in the above-identified patent and that said Letters Patent is hereby corrected as shown below:

```
<210>  15
<211>  4
<212>  PRT
<213>  Artificial

<220>
<223>  Linker

<400>  15

Trp Glu His Asp
1

<210>  16
<211>  4
<212>  PRT
<213>  Artificial

<220>
<223>  Linker

<400>  16

Val Glu His Asp
1
```

UNITED STATES PATENT AND TRADEMARK OFFICE
CERTIFICATE OF CORRECTION

PATENT NO. : 7,354,735 B2
APPLICATION NO. : 10/341979
DATED : April 8, 2008
INVENTOR(S) : Chang et al.

It is certified that error appears in the above-identified patent and that said Letters Patent is hereby corrected as shown below:

```
<210>  17
<211>  4
<212>  PRT
<213>  Artificial

<220>
<223>  Linker

<400>  17

Leu Glu Thr Asp
1

<210>  18
<211>  4
<212>  PRT
<213>  Artificial

<220>
<223>  Linker

<400>  18

Leu Glu His Asp
1
```

UNITED STATES PATENT AND TRADEMARK OFFICE
CERTIFICATE OF CORRECTION

PATENT NO.        : 7,354,735 B2
APPLICATION NO.   : 10/341979
DATED             : April 8, 2008
INVENTOR(S)       : Chang et al.

It is certified that error appears in the above-identified patent and that said Letters Patent is hereby corrected as shown below:

```
<210>  19
<211>  4
<212>  PRT
<213>  Artificial

<220>
<223>  Linker

<400>  19

Ile Glu Thr Asp
1

<210>  20
<211>  16
<212>  PRT
<213>  Artificial

<220>
<223>  Linker

<400>  20

Ser Gly Leu Arg Ser Gly Gly Ile Glu Thr Asp Gly Gly Ser Asn Ser
1               5                   10                  15
```

UNITED STATES PATENT AND TRADEMARK OFFICE
CERTIFICATE OF CORRECTION

| | | |
|---|---|---|
| PATENT NO. | : 7,354,735 B2 | |
| APPLICATION NO. | : 10/341979 | |
| DATED | : April 8, 2008 | |
| INVENTOR(S) | : Chang et al. | |

It is certified that error appears in the above-identified patent and that said Letters Patent is hereby corrected as shown below:

```
<210>  21
<211>  22
<212>  PRT
<213>  Artificial

<220>
<223>  Linker

<400>  21

Ser Gly Leu Arg Ser Gly Gly Ile Glu Thr Asp Gly Gly Ile Glu Thr
1               5                   10                  15

Asp Gly Gly Ser Asn Ser
            20

<210>  22
<211>  6
<212>  PRT
<213>  Artificial

<220>
<223>  Linker
```

UNITED STATES PATENT AND TRADEMARK OFFICE
CERTIFICATE OF CORRECTION

| | |
|---|---|
| PATENT NO. | : 7,354,735 B2 |
| APPLICATION NO. | : 10/341979 |
| DATED | : April 8, 2008 |
| INVENTOR(S) | : Chang et al. |

It is certified that error appears in the above-identified patent and that said Letters Patent is hereby corrected as shown below:

```
<220>
<221>  misc_feature
<222>  (2)..(5)
<223>  Xaa can be any naturally occurring amino acid

<400>  22

Gly Xaa Xaa Xaa Xaa Gly
1               5
<210>  23
<211>  8
<212>  PRT
<213>  Artificial <220>
<223>  Linker <220>
<221>  misc_feature
<222>  (3)..(6)
<223>  Xaa can be any naturally occurring amino acid

<400>  23

Gly Gly Xaa Xaa Xaa Xaa Gly Gly
1               5
```

UNITED STATES PATENT AND TRADEMARK OFFICE
CERTIFICATE OF CORRECTION

| | |
|---|---|
| PATENT NO. | : 7,354,735 B2 |
| APPLICATION NO. | : 10/341979 |
| DATED | : April 8, 2008 |
| INVENTOR(S) | : Chang et al. |

It is certified that error appears in the above-identified patent and that said Letters Patent is hereby corrected as shown below:

```
<210>   24
<211>   14
<212>   PRT
<213>   Artificial

<220>
<223>   Linker

<220>
<221>   misc_feature
<222>   (6)..(9)
<223>   Xaa can be any naturally occurring amino acid

<400>   24

Gly Gly Ser Gly Gly Xaa Xaa Xaa Xaa Gly Gly Ser Gly Gly
1               5                       10

<210>   25
<211>   16
<212>   PRT
<213>   Artificial

<220>
<223>   Linker
```

UNITED STATES PATENT AND TRADEMARK OFFICE
CERTIFICATE OF CORRECTION

PATENT NO. : 7,354,735 B2
APPLICATION NO. : 10/341979
DATED : April 8, 2008
INVENTOR(S) : Chang et al.

It is certified that error appears in the above-identified patent and that said Letters Patent is hereby corrected as shown below:

```
<220>
<221>  misc_feature
<222>  (8)..(11)
<223>  Xaa can be any naturally occurring amino acid

<400>  25

Ser Gly Leu Arg Ser Gly Gly Xaa Xaa Xaa Xaa Gly Gly Ser Asn Ser
1               5                   10                  15

<210>  26
<211>  22
<212>  PRT
<213>  Artificial

<220>
<223>  Linker

<220>
<221>  misc_feature
<222>  (11)..(14)
<223>  Xaa can be any naturally occurring amino acid
```

UNITED STATES PATENT AND TRADEMARK OFFICE
CERTIFICATE OF CORRECTION

PATENT NO.       : 7,354,735 B2
APPLICATION NO.  : 10/341979
DATED            : April 8, 2008
INVENTOR(S)      : Chang et al.

It is certified that error appears in the above-identified patent and that said Letters Patent is hereby corrected as shown below:

```
<400>  26

Ser Gly Leu Arg Ser Gly Gly Ser Gly Gly Xaa Xaa Xaa Xaa Gly Gly
1               5                   10                  15

Ser Gly Gly Ser Asn Ser
            20
```

Signed and Sealed this

Twenty-third Day of December, 2008

JON W. DUDAS
*Director of the United States Patent and Trademark Office*